(12) United States Patent
Jamjanam et al.

(10) Patent No.: US 10,669,264 B2
(45) Date of Patent: Jun. 2, 2020

(54) PROCESS FOR THE PREPARATION OF MACITENTAN

(71) Applicant: Laurus Labs Ltd., Hyderabad (IN)

(72) Inventors: Srivardhana Rao Jamjanam, Hyderabad (IN); Venkata Ramakrishna Murthy Moturu, Hyderabad (IN); Venkata Sunil Kumar Indukuri, Hyderabad (IN); Srihari Raju Kalidindi, Hyderabad (IN); Satyanarayana Chava, Hyderabad (IN)

(73) Assignee: Laurus Labs Limited, Hyderabad (IN)

( * ) Notice: Subject to any disclaimer, the term of this patent is extended or adjusted under 35 U.S.C. 154(b) by 0 days.

(21) Appl. No.: 15/779,374

(22) PCT Filed: Nov. 30, 2016

(86) PCT No.: PCT/IB2016/057203
§ 371 (c)(1),
(2) Date: May 25, 2018

(87) PCT Pub. No.: WO2017/093903
PCT Pub. Date: Jun. 8, 2017

(65) Prior Publication Data
US 2018/0370954 A1 Dec. 27, 2018

(30) Foreign Application Priority Data
Nov. 30, 2015 (IN) .............. 6404/CHE/2015

(51) Int. Cl.
*C07D 403/12* (2006.01)

(52) U.S. Cl.
CPC ................ *C07D 403/12* (2013.01)

(58) Field of Classification Search
CPC ..................................... C07D 403/12
See application file for complete search history.

(56) References Cited

U.S. PATENT DOCUMENTS 8,324,232 B2 * 12/2012 Bolli ............... C07D 403/12
514/274
2014/0309264 A1 * 10/2014 Schaefer ............ C07C 235/54
514/350

FOREIGN PATENT DOCUMENTS

IN 3334/CHE/2014 2/2016
IN 2431/CHE/2015 11/2016

OTHER PUBLICATIONS

Yi et al. Chemical Abstract vol. 165, No. 55508 (Abstract for CN 105622523 Jun. 1, 2016). (Year: 2016).*
Martin H. Bolli et al. "The Discovery of N-[5-(Bromophenyl)-6-[2-[(5-bromo-2-pyrimidinyl)oxy]ethoxy]-4-pyrimidinyl]-N-propylsulfamide (Macitentan), an Orally Active, Potent Dual Endothelin Receptor Antagonist" Journal of Medicinal Chemistry 55, 7849-7861, Aug. 2, 2012.

* cited by examiner

*Primary Examiner* — Emily A Bernhardt
(74) *Attorney, Agent, or Firm* — Blank Rome LLP (57) ABSTRACT

The present invention relates to an improved process for the preparation of macitentan and pharmaceutical acceptable salts thereof. Further present invention also relates to methylene chloride solvate of macitentan and their use in the preparation of pure macitentan.

11 Claims, 4 Drawing Sheets

PROCESS FOR THE PREPARATION OF MACITENTAN

CROSS-REFERENCE TO RELATED APPLICATIONS

This application is a national stage application of and claims the benefit of International Application PCT/IB2016/057203, filed on 30 Nov. 2016, which is based on and claims the benefit of Indian Provisional Application No. 6404/CHE/2015 filed on Nov. 30, 2015, the content of each of which is incorporated by reference herein.

FIELD OF THE INVENTION

The present invention relates to an improved process for the preparation of macitentan and pharmaceutical acceptable salts thereof. Further the present invention also relates to methylene chloride solvate of macitentan and their use in the preparation of pure macitentan.

BACKGROUND OF THE INVENTION

Macitentan is an endothelin receptor antagonist (ERA) and is chemically known as N-[5-(4-bromophenyl)-6-[2-[(5-bromo-2-pyrimidinyl)oxy]ethoxy]-4-pyrimidinyl]-N'-propylsulfamide and represented by the following structural formula (I);

Macitentan is a dual ERA, meaning that it acts as an antagonist of two endothelin (ET) receptor subtypes, $ET_A$ and $ET_B$. Macitentan was approved by US FDA on Oct. 13, 2013 for the treatment of pulmonary arterial hypertension (PAH) and commercially available under the brand name of Opsumit.

Macitentan and process for its general preparation method was disclosed in U.S. Pat. No. 7,094,781. The process for the preparation of macitentan was first exemplified in Journal of Medicinal Chemistry 55, 7849-7861, 2012 and the disclosed process is schematically represented as below:

The above disclosed process has the following disadvantages;

Step b) and step g) involves the use of sodium hydride. In general, sodium hydride is highly flammable and can ignite in air especially upon contact with moisture. Need to carry out sodium hydride reactions under inert atmosphere such as nitrogen or argon gas. The use of sodium hydride in commercial scale is not advisable in safety point of view;

The conversion of compound IV to compound Va in step d) involves the use of highly corrosive phosphoryl chloride under neat conditions at a temperature of about 130° C. and distillation of the highly corrosive phosphoryl chloride after completion of the reaction;

Macitentan obtained by the above process having higher amount un-reacted compound VII as an impurity, which is not easy to remove even after repeated purifications.

IPCOM000236886D journal publication discloses the preparation of amorphous macitentan by the reaction of N-5-(4-bromophenyl)-6-(2-hydroxyethoxy)-4-pyrimidinyl)-N'-propyl-sulfamide with 5-bromo-2-chloropyrimidine in presence of lithium amide in tetrahydrofuran and dimethylformamide. Further WO2016009322 and 3341/MUM/2014 also discloses amorphous form of macitentan and process for its preparation.

WO2014198178 publication discloses crystalline Form II of macitentan as well as methanol, nitromethane and methyl tert-butyl ether solvates of macitentan, process for their preparation and pharmaceutical composition comprising the same. Further this publication designates the crystalline form of macitentan obtained from methanol crystallization as per Journal of Medicinal Chemistry 55, 7849-7861, 2012 as "Form I".

CN105461637A publication discloses crystalline form of macitentan and process for its preparation. The disclosed process involves crystallization of crude macitentan from a solvent selected from methanol, ethanol, isopropanol, diethyl ether, acetonitrile, acetone, methylene chloride, ethyl acetate, n-hexane, n-heptane, petroleum ether or mixture thereof.

CN105461638A publication discloses crystalline Form H of macitentan and process for its preparation. The disclosed process involves crystallization of crude macitentan from ethyl acetate solvent or its mixture with methanol or n-hexane.

CN105622523A publication discloses crystalline form of macitentan and process for its preparation. The disclosed process involves dissolution of macitentan in methylene chloride, subjecting to carbon treatment, filtering and washing the filter cake with hot methanol; concentrating the filtrate up to 0.05-0.5 g/ml; followed by adding methylisobutyl ketone to the concentrate, cooling to room temperature and filtering the crystalline macitentan.

CN105461639A publication discloses a process for purification of macitentan, which involves crystallization of crude macitentan from ethyl acetate or its mixture with methanol or hexane.

CN103819411 publication discloses the preparation of N-(5-(4-bromophenyl)-6-chloro-4-pyrimidinyl)-N'-propyl sulfonamide, which involves the reaction of 5-(4-bromophenyl)-4,6-dichloropyrimidine with N-propylsulfamoyl amide in presence of alkoxy metal compound.

WO2014155304 publication discloses the preparation of N-(5-(4-bromophenyl)-6-(2-hydroxyethoxy)pyrimidine-4-yl)propane-1-sulfamide and the disclosed process represented schematically as follows:

WO2015004265 publication discloses process for the preparation of N-(5-(4-bromo phenyl)-6-(2-hydroxyethoxy) pyrimidine-4-yl)propane-1-sulfamide. The disclosed process involves the reaction of N-(5-(4-bromophenyl)-6-chloropyrimidin-4-yl)-propane-1-sulfamide with ethylene glycol in presence of potassium tertiary butoxide and extracting the obtained N-(5-(4-bromophenyl)-6-(2-hydroxyethoxy) pyrimidine-4-yl)propane-1-sulfamide with MIBK.

WO2015121397 publication discloses the preparation of macitentan and the disclosed process is schematically represented as below.

IN 1724/MUM/2015 publication discloses a process for the preparation of 5-(4-bromophenyl)-4,6-dichloropyrimidine. The disclosed process involves esterification of 4-(bromophenyl)acetic acid with methanol in presence of sulphuric acid to provide methyl (4-bromophenyl)acetate, which on condensation with dimethyl carbonate in presence of sodium methoxide in tetrahydrofuran to provide dimethyl (4-bromophenyl)malonate, which on cyclization with formamide in presence of sodium methoxide in methanol provides 5-(4-bromophenyl)-pyrimidine-4,6-diol followed by chlorination with phosphorous oxychloride provides 5-(4-bromophenyl)-4,6-dichloropyrimidine.

IN 2431/CHE/2015 publication discloses a process for the preparation of macitentan, which involves reaction of N-[5-(4-bromophenyl)-6-chloropyrimidin-4-yl]-N'-propylsulfuric diamide with ethylene glycol in presence of tripotassium phosphate to provide N-[5-(4-bromophenyl)-6-(2-hydroxyethoxy)pyrimidin-4-yl]-N'-propyl sulfuric diamide, which on condensation with 5-bromo-2-chloro pyrimidine in presence of sodium hydroxide, tetrabutylammonium bromide in methylene chloride provides macitentan.

Patent publications CN105272923A and 3334/CHE/2014 also discloses a novel process for the preparation of macitentan.

Macitentan is one of the important drugs, recently approved and available in the market for the treatment of pulmonary arterial hypertension (PAH). Hence it is advantageous to have an improved process for the preparation of macitentan, which avoids the problems allied with the reported processes.

SUMMARY OF THE INVENTION

Accordingly, the present invention provides an improved process for the preparation of macitentan and pharmaceutically acceptable salts thereof.

In one embodiment, the present invention provides an improved process for the preparation of macitentan of formula (I)

and pharmaceutically acceptable salts thereof, comprising the steps of
a) reacting 4-bromophenyl acetic acid alkyl ester of formula (II)

wherein R is $C_{1-4}$ alkyl;
with dialkyl carbonate in presence of a base and a solvent to obtain a compound of formula (III), wherein R is $C_{1-4}$ alkyl;
b) reacting the compound of formula (III) with formamidine or a salt thereof to obtain a compound of formula (IV), c) reacting the compound of formula (IV) with a suitable reactive group source and optionally in presence of a solvent to obtain a compound of formula (V), wherein the Rg represents a reactive group,
d) reacting the compound of formula (V) with N-propylsulfamoyl amide or a salt thereof, in a suitable solvent and optionally in presence of a base to obtain a compound of formula (VI), e) reacting the compound of formula (VI) with ethylene glycol in presence of a base to obtain a compound of formula (VII),

VII f) condensing the compound of formula (VII) with a compound of formula (VIII)

VIII wherein Rg represents a reactive group, in presence of a base and a solvent to obtain macitentan of formula (I); and g) optionally purifying the macitentan of formula (I); wherein the base used in step a) is selected from alkali metal amides such as sodamide, potassium amide; alkali metal oxides such as sodium methoxide, potassium methoxide and mixtures thereof; and the base used in step f) is selected from alkali metal amides such as sodamide, potassium amide and mixtures thereof.

In another embodiment, the present invention provides an improved process for the preparation of macitentan of formula (I), comprising the step of reacting 4-bromophenyl acetic acid alkyl ester of formula (II)

II with dialkylcarbonate in presence of a base and optionally in a suitable solvent to obtain a compound of formula (III), wherein the base used is selected from alkali metal amides selected from sodamide, potassium amide and the like; alkali metal oxides selected from sodium methoxide, potassium methoxide, sodium ethoxide and the like and mixtures thereof.

III

In another embodiment, the present invention provides an improved process for the preparation of macitentan of formula (I), comprising reacting the compound of formula (IV)

IV with phosphoryl chloride in presence of a solvent to obtain a compound of formula (Va), Va wherein phosphoryl chloride used in the ratio of about 4 to about 6 wt/vol w.r. to compound of formula (IV).

In another embodiment, the present invention provides an improved process for the preparation of macitentan of formula (I), comprising condensing a compound of formula (VII)

VII with a compound of formula (VIII)

VIII wherein the Rg represents a reactive group, in presence of a base and a solvent; wherein the base used is selected from alkali metal amides such as sodamide, potassium amide and the like and mixtures thereof.

In another embodiment, the present invention provides a process for the purification of macitentan of formula (I), comprising
  a) dissolving macitentan in a suitable chloro solvent to obtain a solution,
  b) adding suitable alcohol solvent to the step a) solution,
  c) optionally cooling the reaction mass, and
  d) isolating the pure macitentan.

In another embodiment, the present invention provides a process preparation of macitentan of formula (I), comprising the steps of
  a) reacting 4-bromophenyl acetic acid methyl ester of formula (IIa)

IIa with dimethyl carbonate in presence of sodamide in tetrahydrofuran to obtain a compound of formula (IIIa),

IIIa b) reacting the compound of formula (IIIa) with formamidine acetate in presence of sodium methoxide in methanol to obtain a compound of formula (IV),

IV c) reacting the compound of formula (IV) with phosphoryl chloride in acetonitrile to obtain a compound of formula (Va),

Va d) reacting the compound of formula (Va) with N-propylsulfamoyl amide potassium salt in dimethylsulfoxide to obtain a compound of formula (VIa),

VIa e) reacting the compound of formula (VIa) with ethylene glycol in the presence of potassium tertiarybutoxide to obtain a compound of formula (VII),

VII f) condensing the compound of formula (VII) with a compound of formula (VIIIa)

VIIIa in presence of sodamide in tetrahydrofuran to obtain macitentan of formula (I).

In another embodiment the present invention provides methylene chloride solvate of macitentan.

In another embodiment the present invention provides crystalline form of macitentan methylene chloride solvate.

Figure 1:
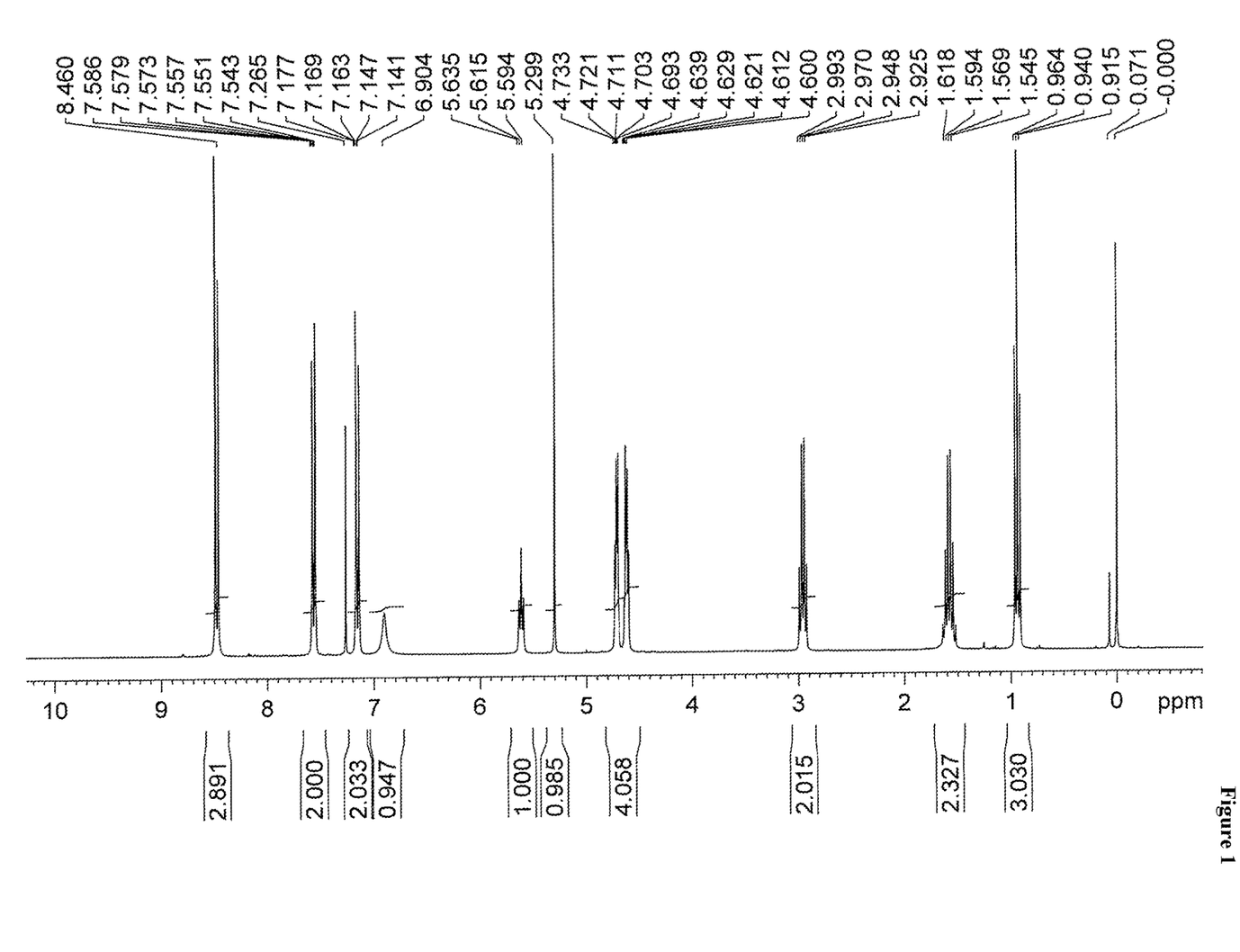
FIG. 1 is the characteristic $^1$H NMR spectrum of macitentan methylene chloride solvate.
Figure 2:
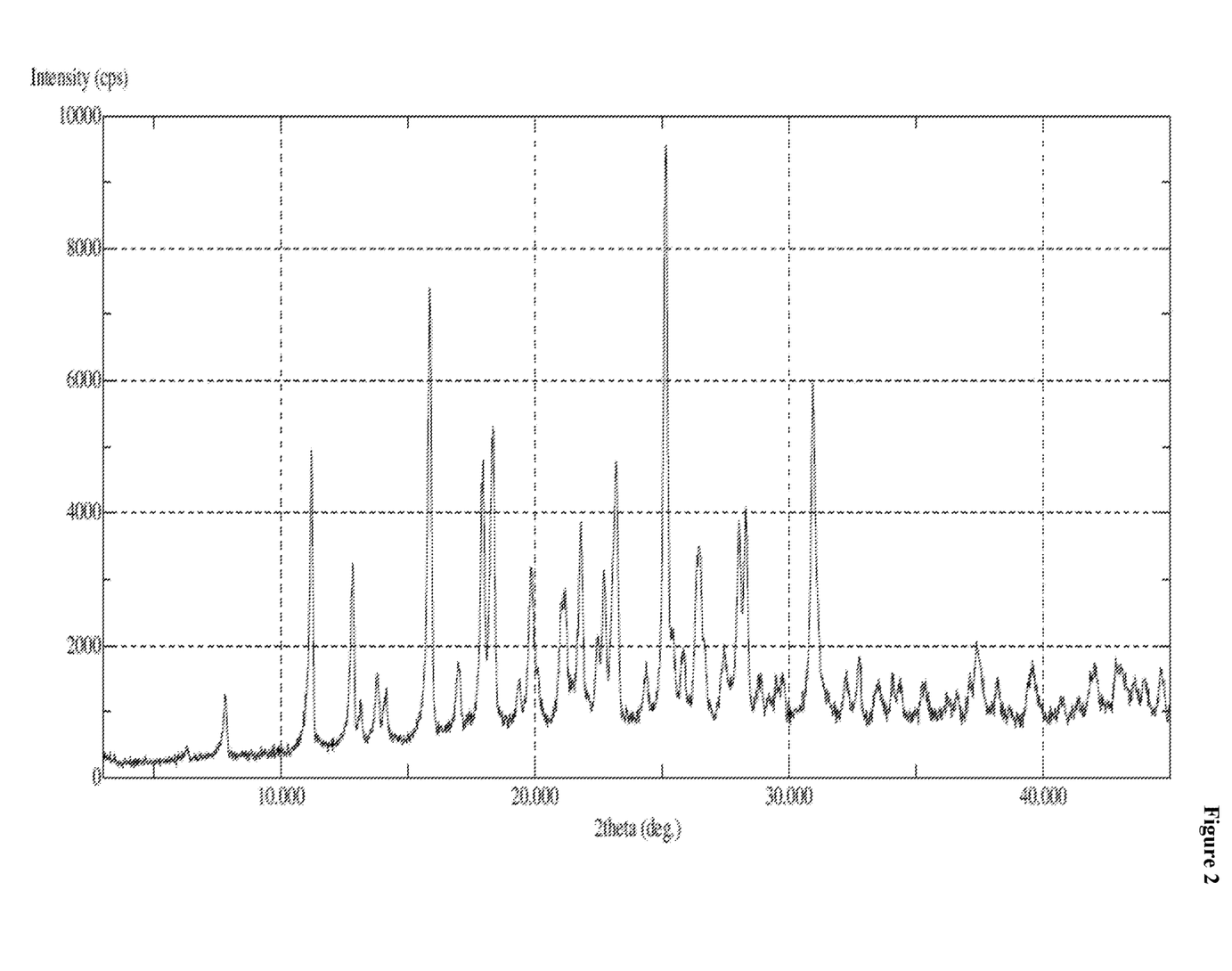
FIG. 2 is the characteristic PXRD pattern of macitentan methylene chloride solvate.
Figure 3:
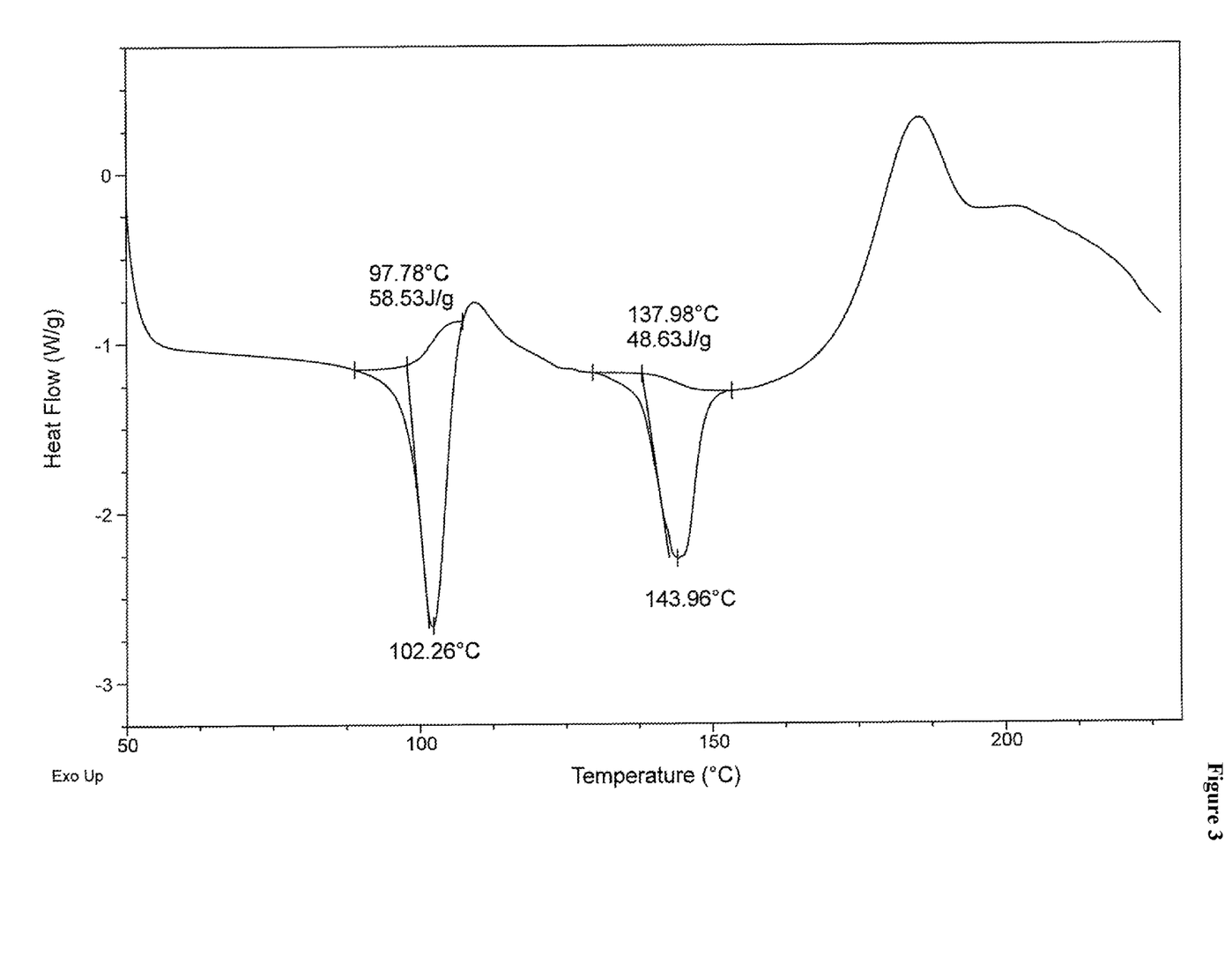
FIG. 3 is the characteristic DSC thermogram of macitentan methylene chloride solvate.
Figure 4:
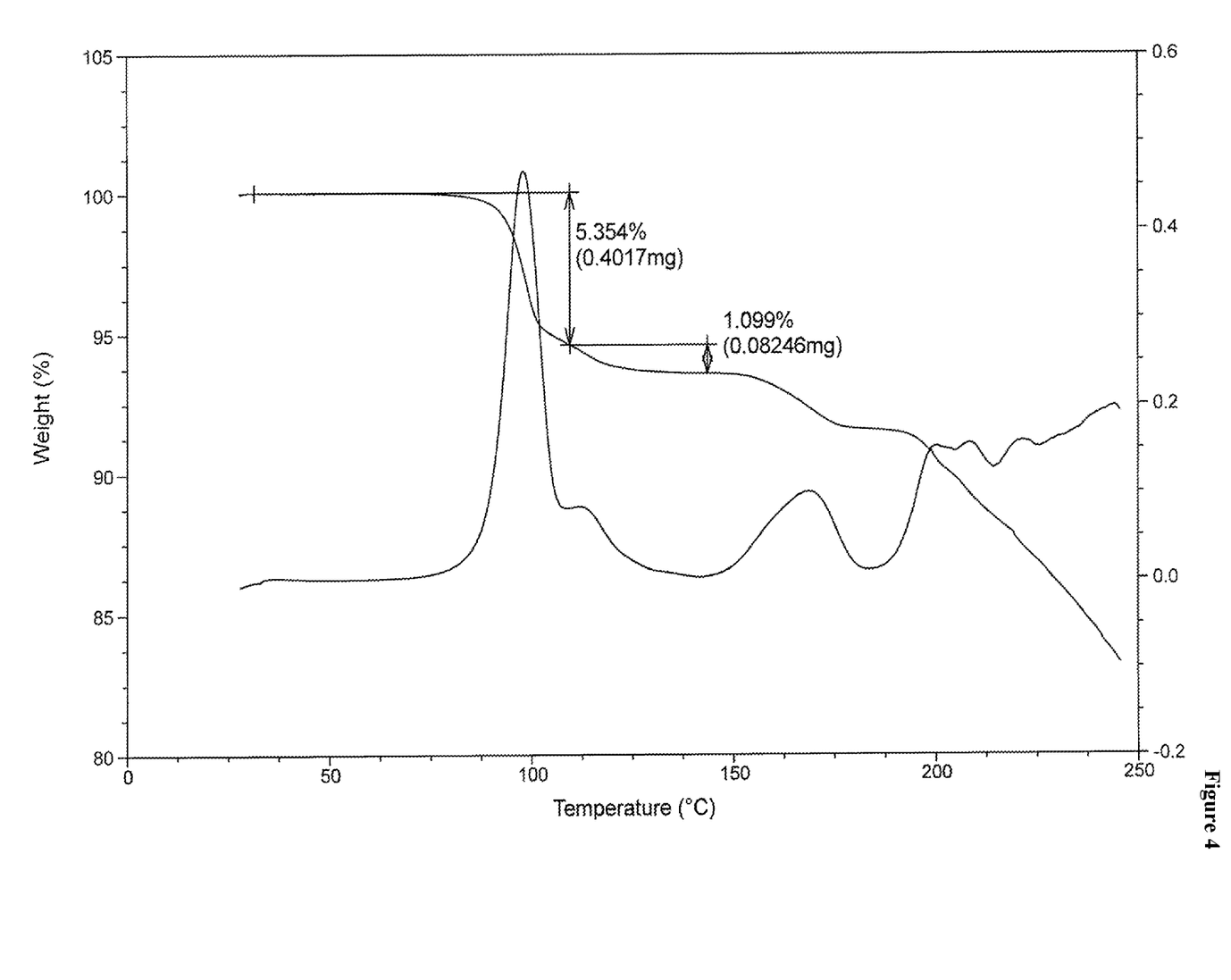
FIG. 4 is the characteristic TGA of macitentan methylene chloride solvate.

In another embodiment, the methylene chloride solvate of macitentan can be characterized by a data selected from one or more of the following; a $^1$H NMR spectrum as depicted in FIG. 1; a PXRD pattern having one or more peaks at about 6.32, 7.80, 11.20, 12.84, 13.14, 13.82, 14.14, 15.86, 16.98, 17.92, 18.32, 19.36, 19.84, 21.20, 21.80, 22.46, 22.70, 23.20, 24.36, 25.14, 25.38, 25.82, 26.48, 27.44, 28.02, 28.30, 28.88, 29.78 and 30.92±0.2° 2θ; a PXRD pattern as depicted in FIG. 2; a differential scanning calorimetry (DSC) as depicted in FIG. 3; a thermo gravimetric analysis (TGA) as depicted in FIG. 4; and combinations of these data.

In another embodiment, the present invention provides a process for the preparation of methylene chloride solvate of macitentan, which comprises dissolving, or slurrying or exposing macitentan in methylene chloride at a suitable temperature; and isolating the methylene chloride solvate of macitentan.

In another embodiment, the present invention provides pharmaceutical composition comprising macitentan prepared according to the processes of the present invention and at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

In one embodiment, the present invention provides an improved process for the preparation of macitentan of formula (I)

and pharmaceutically acceptable salts thereof, comprising the steps of a) reacting 4-bromophenyl acetic acid alkyl ester of formula (II)

wherein R is $C_{1-4}$ alkyl;

with dialkyl carbonate in presence of a base and a solvent to obtain a compound of formula (III), wherein R is $C_{1-4}$ alkyl;

b) reacting the compound of formula (III) with formamidine or a salt thereof to obtain a compound of formula (IV), c) reacting the compound of formula (IV) with a suitable reactive group source and optionally in presence of a solvent to obtain a compound of formula (V), wherein Rg represents a reactive group, d) reacting the compound of formula (V) with N-propylsulfamoyl amide or a salt thereof, in a suitable solvent and optionally in presence of a base to obtain a compound of formula (VI), e) reacting the compound of formula (VI) with ethylene glycol in the presence of a base to obtain a compound of formula (VII).

f) condensing the compound of formula (VII) with a compound of formula (VIII)

wherein Rg represents a reactive group, in the presence of a base and a solvent to obtain macitentan of formula (I); and g) optionally purifying the macitentan of formula (I);

wherein in the base used in step a) is selected from alkali metal amides such as sodamide, potassium amide and the like; alkali metal oxides such as sodium methoxide, potassium methoxide and the like; and mixtures thereof; and the base used in step f) is selected from alkali metal amides such as sodamide, potassium amide and the like and mixtures thereof.

The starting compound 4-bromophenyl acetic acid alkyl ester of formula (II) of the present invention is commercially available or can be prepared by esterification of 4-bromophenyl acetic acid using suitable alcohol and thionyl chloride or by the methods known in the art.

In the forgoing process, the step a) of reacting the 4-bromophenyl acetic acid alkyl ester of formula (II), wherein R is $C_{1-4}$ alkyl such as methyl, ethyl, propyl and the like; preferably methyl; with dialkylcarbonate such as dimethylcarbonate or diethylcarbonate; preferably dimethylcarbonate, is carried out in presence of a base and a solvent to obtain a compound of formula (III). Preferably the suitable base used is selected from sodamide, potassium amide, sodium methoxide, potassium methoxide and the like and mixtures thereof; more preferably sodamide. The solvent used is selected from di-tert-butylether, diethylether, diisopropylether, di-n-butylether, 1,4-dioxane, methyltert-butylether, ethylisoproylether, ethyltert-butylether, tetrahydrofuran, 2-methyl tetrahydrofuran, anisole, dimethoxyethane and the like and mixtures thereof; preferably tetrahydrofuran.

The step a) reaction may be advantageously carried out at a suitable temperature of about 20° C. to about reflux temperature. Preferably, the reaction is carried out at a temperature of about 35° C. to about 65° C.; more preferably at about 50-65° C. The reaction is allowed to stir for a sufficient period of time from about 30 min to until completion of the reaction, preferably for 1-2 hrs.

Optionally the compound of formula (III) obtained in step a) can be further purified using ester and hydrocarbon solvents. Preferably, the purification is carried out by mixing or suspending the crude compound of formula (III) in a suitable ester solvent such as ethylacetate, isopropyl acetate and the like and mixture thereof; preferably ethyl acetate; heating the suspension to about 35-55° C., preferably about 45-50° C.; adding a suitable hydrocarbon solvent such as toluene, hexane, heptane, cyclohexane and the like; preferably heptane; and isolating the pure compound of formula (III) by cooling followed by filtration.

The reported process for the preparation of compound of formula (II) involves the use sodium hydride as a base in tetrahydrofuran and the reaction carried out at a temperature of about 25-40° C. for about 24 to 70 hrs. Sodium hydride is highly flammable and can ignite in air especially upon contact with moisture. It is difficult to handle at commercial scale and having safety concerns. The present inventors surprisingly found that use of sodamide in place of sodium hydride, not only avoids the handling issues associated with sodium hydride as well as the reduced the time cycle of about 1-2 hrs.

In the forgoing process, the step b) of reacting the compound of formula (III) with formamidine or a salt thereof, preferably hydrochloride or acetate salts; can be carried out in presence of a base and a solvent to obtain a compound of formula (IV). The suitable base used herein includes, but are not limited to alkali metal hydroxides such as sodium hydroxide, potassium hydroxide, lithium hydroxide and the like; alkali metal alkoxides such as sodium methoxide, sodium ethoxide, potassium methoxide, potassium ethoxide, lithium methoxide, lithium ethoxide, sodium tert-butoxide, potassium tert-butoxide, sodium tert-pentoxide and the like; and mixtures thereof; preferably sodium methoxide; and the suitable solvent used herein is selected from methanol, ethanol, isopropanol, butanol and the like and mixtures thereof; preferably methanol.

The step b) reaction may be advantageously carried out at a temperature of about 20° C. to about reflux temperature of the solvent, preferably at about 25° C. to about 35° C. for a sufficient period of time to complete the reaction, preferably for 2 to 8 hrs.

In the forgoing process, the step c) of reacting the compound of formula (IV) with a suitable reactive group source such as $POCl_3$, $PCl_3$, $PCl_5$, $PBr_3$, $POBr_3$ or mixtures thereof, can be carried out in presence or absence of a solvent and a base to obtain a compound of Formula (V), wherein Rg represents a reactive group such as chlorine or bromine atom. Preferably the reaction is carried out in presence of a solvent and base. The suitable solvent used herein selected from acetonitrile, propionitrile, butyronitrile, isobutyronitrile, benzonitrile, chloroform, 1,2-dichloroethane, toluene, xylene and the like and mixtures thereof; preferably acetonitrile; the suitable base used herein is selected from triethylamine, tributylamine, diisopropylethylamine, diethylamine, N-methylmorpholine, pyridine, 4-(N,N-dimethylamino) pyridine, N,N-dimethylaniline, N,N-diethylaniline and mixtures thereof; preferably triethylamine. The reactive group source such as phosphoryl chloride ($POCl_3$) is used in the ratio of 4 to 6 wt/vol with respect to the formula (IV).

The reported process for the preparation of formula (V) involves the reaction of formula (IV) with phosphoryl chloride in presence of N,N-dimethylaniline in neat condition at 130° C. and further involves distillation of phosphoryl chloride in the course of product isolation. Phosphoryl chloride is highly corrosive and distillation of huge volumes of the same lead to safety concerns, particularly on commercial scale operations. The present inventors have surprisingly found that less volume of phosphoryl chloride such as 4-6 volumes against 13 volumes as reported in the art, along with acetonitrile as reaction solvent, are enough to complete the reaction even at lower temperatures of about 80-85° C. against 130° C. Further present inventors isolating the product simply by quenching the reaction mass with aqueous hydrochloric acid and avoids distillation of reaction mass comprising phosphoryl chloride, thereby avoids the problem associated with prior art process.

The step c) reaction may be advantageously carried out at a temperature of about 70° C. to about 90° C., preferably at about 80-85° C. for sufficient period of time to complete the reaction, preferably for 4 to 14 hrs.

In the forgoing process, the step d) of reacting the compound of formula (V), wherein Rg represents a reactive group such as chlorine or bromine atom with N-propylsulfamoyl amide or a salt thereof, such as sodium, potassium, lithium and the like; in a suitable solvent and optionally in presence of a base to obtain a compound of formula (VI). The suitable solvent used herein is selected from dimethylsulfoxide, dimethylformamide, dimethylacetamide, acetonitrile, chlorobenzene, isopropylacetate, tetrahydrofuran, dioxane or mixtures thereof; preferably dimethylsulfoxide; The suitable base used herein selected from sodium tert-butoxide, potassium tert-butoxide, sodium hydride, potassium hydride, sodium methoxide, potassium methoxide, sodium ethoxide, triethyl amine, ethyldiisopropyl amine. Preferably the compound of formula (V) reacts with N-propyl sulfamoyl amide potassium salt in presence of a solvent without any additional base.

The step d) reaction may be advantageously carried out at a temperature of about 20° C. to about reflux temperature of the solvent, preferably at about 20-40° C. for sufficient period of time to complete the reaction, preferably for 6-12 hrs.

In the forgoing process, the step e) of reacting the compound of formula (VI), wherein Rg represents a reactive group such as chlorine or bromine atom, with ethylene glycol can be carried out in presence of a suitable base to obtain a compound of formula (VII). Preferably the suitable base used herein include, but are not limited to alkali metal hydroxides such as sodium hydroxide, potassium hydroxide, lithium hydroxide and the like; alkali metal alkoxides such as sodium methoxide, sodium ethoxide, potassium methoxide, potassium ethoxide, lithium methoxide, lithium ethoxide, sodium tert-butoxide, potassium tert-butoxide, sodium tert-pentoxide and the like; alkali metal hydrides such as sodium hydride, potassium hydride and the like; carbonate such as sodium carbonate, potassium carbonates and the like; alkali metal amides such as sodamide, potassium amide and the like; and mixtures thereof; more preferably the base is selected from sodium hydroxide, potassium hydroxide, sodium methoxide, sodium ethoxide, potassium tert-butoxide, sodium carbonate, potassium carbonate, sodamide, potassium amide and mixtures thereof; most preferably potassium tert-butoxide.

Preferably, the addition of base in the present invention can be done by lot-wise manner rather than in a single lot as in prior art and thereby reduces the time cycle of the reaction compared to the known process.

Optionally the compound of formula (VII) obtained is step d) is further purified by recrystallization from suitable alcohol solvents such as methanol, ethanol, isopropanol and the like and mixtures thereof; preferably methanol.

The step d) reaction may be advantageously carried out at a temperature of about 25° C. to be about reflux temperature of the solvent, preferably at about 75° C. to about 100° C. for sufficient period of time to complete the reaction, preferably for 2-10 hrs.

In the forgoing process, the step f) of condensing the compound of formula (VII) with a compound of formula (VIII), wherein Rg represents a reactive group such as a chlorine or a bromine atom, or a methylsulfonyl or ethylsulfonyl group; can be carried out in presence of a base and solvent to obtain macitentan of formula (I). Preferably the suitable base used is selected from sodamide, potassium amide and the like and mixtures thereof; more preferably sodamide; the suitable solvent used is selected from di-tert-butylether, diethylether, diisopropylether, di-n-butylether, 1,4-dioxane, methyltert-butylether, ethylisoproylether, ethyltert-butylether, tetrahydrofuran, 2-methyl tetrahydrofuran, anisole, dimethoxyethane, dimethylformamide and mixtures thereof; preferably tetrahydrofuran.

The step f) reaction may be advantageously carried out at a temperature of about 25° C. to about reflux temperature of the solvent, preferably at about 40° C. to about 55° C. for sufficient period of time to complete the reaction, preferably for 1.5 to 4 hrs.

The reported process involves the reaction of formula (VII) with 5-bromo-2-chloropyrimidine in presence of sodium hydride in tetrahydrofuran at 60-65° C. for about 2-3 hrs. Sodium hydride is highly flammable and can ignite in air especially upon contact with moisture, it is difficult to handle at commercial scale and having safety concerns. The present inventors have surprisingly found that use of sodamide in place of sodium hydride avoids the handling issues associated with sodium hydride.

In the forgoing process, the step g) of purification of macitentan comprises dissolving macitentan in a chloro solvent followed by adding alcohol solvent. The suitable chloro solvent used herein is selected from methylene chloride, ethylene dichloride, carbon tetrachloride, chloroform and mixtures thereof; preferably methylene chloride; the suitable alcohol solvent used is selected from methanol, ethanol, isopropanol, n-butanol; preferably methanol.

In another embodiment, the present invention provides an improved process for the preparation of macitentan of formula (I), comprising condensing the compound of formula (VII)

with a compound of formula (VIII)

Wherein the Rg represents a reactive group such as a chlorine or a bromine atom, or a methylsulfonyl or ethylsulfonyl group, in the presence of a base and a solvent to obtain macitentan of formula (I); wherein the base used is selected from alkali metal amides such as sodamide, potassium amide and the like and mixtures thereof.

In another embodiment, the present invention provides a process for the purification of macitentan of formula (I), comprising a) dissolving macitentan in a suitable chloro solvent to obtain a solution,
b) adding suitable alcohol solvent to the step a) solution,
c) optionally cooling the reaction mass, and
d) isolating the pure macitentan.

In forgoing purification process, dissolution of macitentan in chloro solvent in step a) is carried out at a temperature of about 35° C. to about 40° C.; the suitable chloro solvent used herein is selected from methylene chloride, ethylene dichloride, carbon tetrachloride, chloroform and mixtures thereof; preferably methylene chloride; the addition of suitable alcohol solvent in step b) is carried out at a temperature of about 35° C. to about 40° C.; the suitable alcohol solvent used herein is selected from methanol, ethanol, isopropanol, n-butanol and mixtures thereof; preferably methanol; step b) further comprises heating the reaction mass to about 40° C. to about 45° C. and stirring for sufficient period of time; preferably for 30-45 mins; the reaction mass in step c) is cooled to less than 35° C.; and isolating the pure macitentan in step d) done by filtration.

The purification of macitentan of the present invention comprise of the following steps;

a) dissolving macitentan in suitable chloro solvent at a temperature of about 35-40° C.,
b) adding suitable alcohol solvent to the step a) solution at about 35-40° C.,
c) heating the reaction mixture to about 40-45° C.; and
d) isolating the pure macitentan by cooling the reaction mass followed by filtration.

Macitentan prepared according to the process disclosed in Journal of Medicinal Chemistry 55, 7849-7861, 2012 is contaminated with higher amount of un-reacted compound (VII) as impurity, which is not easy to remove even after repeated purifications. The repetition of the reported process and multiple purifications using methanol as solvent by the present inventors identified that about 0.2% of compound (VII) as impurity, which product is not acceptable according to ICH guidelines. In contrast, purification process of the present invention is using mixture of chloro solvent and alcohol solvents yields macitentan having compound of formula (VII) in less than 0.15% by HPLC.

The macitentan obtained by above purification process is having less than 0.15% by HPLC of compound of formula VII; preferably less than 0.10% by HPLC.

The macitentan obtained by the present invention having purity greater than 99.90% by HPLC; preferably greater than 99.95% by HPLC and more preferably greater than 99.97%.

In another embodiment the present invention provides methylene chloride solvate of macitentan.

In another embodiment the present invention provides crystalline macitentan methylene chloride solvate.

In another embodiment, the present invention provides crystalline macitentan methylene chloride solvate characterized by $^1$H NMR spectrum as depicted in FIG. 1.

In another embodiment, the present invention provides crystalline macitentan methylene chloride solvate characterized by a PXRD pattern having one or more peaks at about 6.32, 7.80, 11.20, 12.84, 13.14, 13.82, 14.14, 15.86, 16.98, 17.92, 18.32, 19.36, 19.84, 21.20, 21.80, 22.46, 22.70, 23.20, 24.36, 25.14, 25.38, 25.82, 26.48, 27.44, 28.02, 28.30, 28.88, 29.78 and 30.92±0.2°2θ.

In another embodiment, the present invention provides crystalline macitentan methylene chloride solvate characterized by a powder X-Ray diffraction (PXRD) pattern as depicted in FIG. 2.

In another embodiment, the present invention provides crystalline macitentan methylene chloride solvate characterized by a differential scanning calorimetry (DSC) as depicted in FIG. 3.

In another embodiment, the present invention provides crystalline macitentan methylene chloride solvate characterized by a thermo gravimetric analysis (TGA) as depicted in FIG. 4.

In another embodiment, the methylene chloride solvate of macitentan can be characterized by data selected from one or more of the following; a $^1$H NMR spectrum as depicted in FIG. 1; a PXRD pattern having one or more peaks at about 6.32, 7.80, 11.20, 12.84, 13.14, 13.82, 14.14, 15.86, 16.98, 17.92, 18.32, 19.36, 19.84, 21.20, 21.80, 22.46, 22.70, 23.20, 24.36, 25.14, 25.38, 25.82, 26.48, 27.44, 28.02, 28.30, 28.88, 29.78 and 30.92±0.2° 2θ; a PXRD pattern as depicted in FIG. 2; a differential scanning calorimetry (DSC) as depicted in FIG. 3; a thermo gravimetric analysis (TGA) as depicted in FIG. 4; and combinations of these data.

In another embodiment, the present invention provides a process for the methylene chloride solvate of macitentan, comprises dissolving, or slurrying or exposing macitentan in methylene chloride at a temperature of about 25° C. to 30° C.; and isolating the methylene chloride solvate of macitentan.

In the aforementioned process, dissolving or slurrying of macitentan in methylene chloride can be carried out at a suitable temperature of about 25° C. to about 30° C. for 30 mins to 1 hr. Then the isolation of methylene chloride solvate of macitentan from the reaction mass can be carried out by any conventional techniques known in the art, for example cooling the reaction mass to 0-5° C., filtration followed by drying. The step of exposing may be carried out by exposing the macitentan under methylene chloride atmosphere for about 10 minutes to about 24 hours at ambient temperature.

In another embodiment, methylene chloride solvate of macitentan can be used as intermediate in the preparation of therapeutically acceptable form of macitentan.

In another embodiment, the present invention provides a process for the preparation of macitentan, comprising de-solvating methylene chloride solvate of macitentan by means drying the solid methylene chloride solvate of macitentan at 35-40° C. under atmospheric or reduced pressure; or treating the methylene chloride solvate of macitentan in an alcoholic solvent at a temperature of about 25° C. to about reflux.

In another embodiment, the present invention provides a pharmaceutical composition comprising a therapeutically effective amount of macitentan or pharmaceutically acceptable salts thereof, particularly macitentan of the invention with at least one pharmaceutically acceptable excipient.

The X-Ray powder diffraction can be measured by an X-ray powder diffractometer equipped with a Cu-anode ([k]=1.54 Angstrom), X-ray source operated at 30 kV, 15 mA. The sample was analysed using the following instrument parameters: measuring range=3-45° 2θ; step width=0.020°; and scan speed=5°/minute.

All DSC data reported herein were analysed in hermitically sealed aluminium pan with pin hole, with a blank hermitically sealed aluminium pan with pin hole as the reference and were obtained using DSC (DSC Q200, TA instrumentation, Waters) at a scan rate of 10° C. per minute with an Indium standard.

All TGA data reported herein were analysed using TGA Q500 V 20.2 build 27 in platinum pan with a temperature rise of about 10° C./min in the range of about 30° C. to about 250° C.

$^1$H-NMR spectra recorded on a Bruker Avance-II 300 MHz spectrometer at a $^1$H Larmor frequency of 300.131 MHz.

The following examples and drawings are provided by way of illustration only, and are not intended to be limiting of the present invention. Further, the present invention covers all the possible combinations of particular and preferred embodiments indicated herein.

EXAMPLES

Example-1: Preparation of 2-(4-bromophenyl) malonic acid dimethyl ester (Formula IIIa)

To a solution of 4-bromophenylacetic acid (100 g) in methanol (500 mL), thionyl chloride (40 mL) was added at 0-5° C. under nitrogen atmosphere. The temperature of the reaction mass was raised to 25-30° C. and stirred for 30 mins. The solvent from the reaction mass was distilled off completely under vacuum at 40-45° C. The obtained mass was dissolved in ethyl acetate (500 mL) at 25-30° C. and then washed with 5% aqueous sodium bicarbonate, water followed by 35% aqueous sodium chloride solution. The organic and aqueous layers were separated and the separated organic layer was dried over anhydrous sodium sulphate. The organic layer was filtered, washed with ethyl acetate and the solvent from filtrate was distilled off completely under vacuum at 45-50° C. The obtained residue and dimethyl carbonate (159.6 mL) in tetrahydrofuran (400 mL) was slowly added to a mixture of tetrahydrofuran (600 mL) and sodamide (54.4 g) at 35-40° C. The reaction mass was cooled to 25-30° C. and stirred for an hour. The reaction mass was cooled to 0-5° C. and pH was adjusted to 6.5 with aqueous hydrochloric acid. The reaction mass temperature was raised to 25-30° C. and solvent from the reaction mass was distilled of under vacuum at below 45-50° C. Ethyl acetate (1000 mL), 1N HCl (500 mL) was added to the reaction mass at 25-30° C. Organic and aqueous layers were separated; extracted the aqueous layer with ethyl acetate. Organic layer was washed with 5% aqueous sodium bicarbonate solution and extracted the aqueous sodium bicarbonate layer with ethyl acetate. Organic layers were combined and washed with water followed by sodium chloride solution at 25-30° C. The solvent from the organic layer was distilled off completely under vacuum at below 45° C. n-heptane (400 mL) was added to the obtained residue and stirred for 30 mins at 40-45° C. The reaction mass was cooled to 25-35° C. and stirred for 45 mins. The reaction mass was further cooled to 0-5° C. and stirred for 2 hrs. The solid obtained was filtered, washed with chilled n-heptane and dried at 40-45° C. for 6 hrs to get the title compound. Yield: 98 g; Purity by HPLC: 95%

Example-2: Preparation of 2-(4-bromophenyl) malonic acid dimethyl ester (Formula IIIa)

To a solution of 4-bromophenylacetic acid (100 g) in methanol (500 mL), thionyl chloride (40 mL) was added at 0-5° C. The temperature of the reaction mass was raised to 25-35° C. and stirred for 30 mins. The solvent from the reaction mass was distilled off completely under vacuum at 40-45° C. The obtained mass was dissolved in ethyl acetate (500 mL) at 25-30° C. and then washed with 5% aqueous sodium bicarbonate, water followed by 35% aqueous sodium chloride solution. The organic and aqueous layers were separated and organic layer was dried over anhydrous sodium sulphate. The organic layer was filtered, washed with ethyl acetate and the solvent from filtrate was distilled off completely under vacuum at 45-50° C. The obtained residue was dissolved in tetrahydrofuran (400 mL) at 25-35° C. and dimethyl carbonate (159.6 mL) was added to it. The obtained reaction mass was added to mixture of sodamide (54.4 g) in tetrahydrofuran (600 mL) at 53-65° C. then stirred for 90 mins. The reaction mass was cooled to 0-5° C. and pH was adjusted to 6.5 with aqueous hydrochloric acid. The reaction mass temperature was raised to 25-30° C., stirred for 10 mins and organic and aqueous layers were separated. Organic layer was distilled off under vacuum at below 45° C. Ethyl acetate (500 mL) followed by 1N HCl (500 mL) was added to the reaction mass at 25-30° C. and stirred for 10 mins. The organic and aqueous layers were separated; organic layer washed with sodium chloride and then dried over anhydrous sodium sulphate then filtered. The solvent from filtrate was distilled off completely under vacuum at below 45° C. n-Heptane (100 mL) was added to the residue, stirred and again distilled off completely. Heptane (400 ml) was added to the reaction mass, stirred for 45 mins at below 50° C. The reaction mass was cooled to 25-35° C. and stirred for 45 mins. The reaction mass was further cooled to 0-5° C. and stirred for 2 hrs. The solid obtained was filtered, washed with chilled n-heptane and suck dried. Ethyl acetate (50 mL) was added to the above wet material and heater to 45-50° C. and stirred for 20 mins. Heptane (400 mL) was added to the reaction mass at 45-50° C. then the reaction mass was cooled to 25-35° C. and stirred for 90 mins. The precipitated solid was filtered, washed with n-heptane and dried under vacuum at 40-45° C. for 3-4 hrs to get pure title compound. Yield: 95 g; Purity by HPLC: 99.6%

Example-3: Preparation of 5-(4-bromophenyl)-pyrimidine-4,6-diol (Formula IV)

A solution of 2-(4-bromophenyl) malonic acid dimethyl ester (Formula III) (100 g) in methanol (1500 ml) was added to pre-cooled 25% sodium methoxide solution in methanol (240 mL) at 0-5° C. over a period of 60 mins under nitrogen atmosphere and stirred for 15 mins. Formamidine acetate (47.1 g) was added at 0-5° C. Then reaction mass temperature was raised to 25-30° C. and stirred for 6 hrs Aqueous hydrochloric acid (2N, 1000 mL) was added to the reaction mass at 25-30° C. for 90 mins, cooled to 0-5° C. and stirred for 30 mins. The pH of the reaction mass was adjusted to 4 using aqueous sodium hydroxide at 0-5° C. and stirred for 15 mins. The solid obtained was filtered, washed with water followed by acetone and suck dried. Acetone (300 mL) was added to the wet compound and stirred for 1 hr at 25-35° C. The reaction mass was filtered, washed with acetone and dried at 60-65° C. for 12 hrs to get the title compound. Yield: 80 g; Purity by HPLC: 99.5%.

Example-4: Preparation of 5-(4-bromophenyl)-4,6-dichloro-pyrimidine (Formula Va)

Triethyl amine (130 mL) was added to a mixture of 5-(4-bromophenyl)-pyrimidine-4,6-diol (100 g), phosphoryl chloride (400 mL) and acetonitrile (600 mL) at 25-35° C. under nitrogen atmosphere for a period of 60 mins. The reaction mass was heated to 80-85° C. and stirred for 4 hrs. The reaction mass was distilled off under vacuum at below 75° C. followed by stripped off with acetonitrile. The reaction mass was cooled to 10-15° C., water (500 mL) was added and stirred for 30 mins. Aqueous hydrochloric acid (2N, 500 ml) was added to the reaction mass at 10-15° C. and stirred for 30 mins. The solid obtained was filtered, washed with water and dried under vacuum at 40-45° C. for 6 hrs to get the title compound. Yield: 100 g; purity by HPLC: 99.0%

Example-5: Preparation of 5-(4-bromophenyl)-4,6-dichloro-pyrimidine (Formula Va)

Triethyl amine (130 mL) was added to a mixture of 5-(4-bromophenyl)-pyrimidine-4,6-diol (100 g), phosphoryl chloride (400 mL) and acetonitrile (600 mL) at 25-35° C. under nitrogen atmosphere for a period of 60 mins. The reaction mass was heated to 80-85° C. and stirred. After reaction completion, the reaction mass was cooled to 25-35° C. and added to the pre-cooled solution of aqueous hydrochloric acid (1N, 1500 ml) at 10-20° C. and then stirred for 2 hrs. The solid obtained was filtered, washed with water and dried under vacuum at 40-45° C. for 6 hrs to get the title compound. Yield: 98 g; purity by HPLC: 99.8%

Example-6: Preparation of N-5-(4-bromophenyl)-6-chloro-4-pyrimidinyl-N'-propyl sulfamide (Formula VIa)

To a solution of 5-(4-bromophenyl)-4,6-dichloro-pyrimidine (100 g) in dimethyl sulfoxide (700 ml), potassium(N- propylsulfamoyl)amide (145 g) was added at 25-30° C. under nitrogen atmosphere and stirred for 10 hrs. After reaction completion, pH of the reaction mass was adjusted to 2-3 using aqueous hydrochloric acid at 25-30° C. and stirred for 75 mins. The solid obtained was filtered, washed with water and suck dried under vacuum. Methanol (3500 ml) was added to the above compound and heated to reflux temperature then stirred for an hour at reflux. The reaction mass was distilled upto 450-550 mL remained in the flask. The reaction mass was cooled to 25-30° C., stirred for 75 mins then further cooled to 0-5° C. and stirred for 75 mins. The obtained solid was filtered, washed with methanol and dried under vacuum at 50-55° C. for 4 hrs to get the title compound. Yield: 110 g; Purity by HPLC: 99.10%.

Example-7: Preparation of N-5-(4-bromophenyl)-6-(2-hydroxyethoxy)-4-pyrimidinyl-N'-propylsulfamide (Formula VII)

Ethylene glycol (700 mL) was added to N-5-(4-bromophenyl)-6-chloro-4-pyrimidinyl-N'-propylsulfamide (100 g) under nitrogen atmosphere at 25-30° C. Potassium tert-butoxide (249 g) was added in lots to the above reaction mass at 25-35° C., then heated to 85-90° C. and stirred for 6 hrs at reflux. The reaction mass was cooled to 25-35° C. and potassium tert-butoxide (55 g) was added in lots to the reaction mass at 25-35° C. The reaction mass was heated to reflux and stirred for 4 hrs at reflux temperature. The reaction mass was cooled to 25-35° C. and water (300 ml) followed by 1N aqueous hydrochloric acid (1500 ml) was added to it and stirred for an hour. The solid obtained was filtered, washed with water and suck dried. Methanol (300 mL) was added to the above solid and heated the reaction mass to 65-70° C. then stirred for 10 mins. The reaction mass was cooled to 25-30° C. and stirred for an hour. The solid obtained was filtered, washed with chilled methanol and dried at 50-55° C. under vacuum for 6 hrs to get the title compound. Yield: 91 g; Purity by HPLC: 99.0%

Example-8: Preparation of N-5-(4-bromophenyl)-6-(2-hydroxyethoxy)-4-pyrimidinyl-N'-propylsulfamide (Formula VII)

The title compound of formula VII was prepared in accordance with example 5, except that final purification in methanol was carried out at 50-60° C. instead of 65-70° C. Yield: 87 g; purity by HPLC: 99.3%

Example-9: Preparation of Macitentan (Formula I)

A solution of N-5-(4-bromophenyl)-6-(2-hydroxyethoxy)-4-pyrimidinyl-N'-propyl sulfamide (100 g) in tetrahydrofuran (500 mL) was added to sodamide (13.6 g) in tetrahydrofuran (1500 mL) at 25-30° C. over a period of 45 min and stirred for 10 min. 5-bromo-2-chloropyrimidine (45 g) was added to the above reaction mass at 25-30° C. and stirred for 10 mins. The reaction mass was heated to 60-65° C. and stirred for 2.5 hrs. The reaction mass was then cooled to 25-30° C.; sodamide (13.6 g) and 5-bromo-2-chloropyrimidine (45 g) was added to the reaction mass. The reaction mass was heated to 60-65° C. and stirred for 2.5 hrs. The reaction mass was cooled to 25-30° C. and pH was adjusted to 2-2.5 with aqueous hydrochloric acid and stirred for 15 mins. The solvent from the reaction mass was distilled off under vacuum at 45° C. Methylene chloride (1000 mL) was added to the reaction mass and stirred for 15 mins. The organic and aqueous layers were separated and the aqueous layer extracted with methylene chloride. Organic layers were combined, washed with water and 5% sodium bicarbonate solution followed by water and sodium chloride solution. The organic layer was concentrated completely under vacuum at below 45° C. Then the reaction mass was cooled to 25-30° C., added methylene chloride (150 mL) and heated to 35-40° C. for complete dissolution. Methanol (1000 mL) was added to the reaction mass at 35-40° C., heated to 65-70° C. and stirred for 45 min at reflux. The reaction mass was cooled to 25-30° C. and stirred for an hour. The solid obtained was filtered, washed with methanol and suck dried. Methylene chloride (180 mL) was added to the above solid and heated to 35-40° C. and stirred for 30 mins. Methanol (1100 mL) was added to the reaction mass at 35-40° C. and stirred for 45 mins at 40-45° C. The reaction mass was cooled to 25-30° C. and stirred for an hour. The solid obtained was filtered, washed with methanol and dried at 50° C. for 6 hrs to get the title compound. Yield: 92 g; Purity by HPLC: 99.97%; Formula (VII): <0.1%

Example-10: Preparation of Macitentan (Formula I)

A solution of N-5-(4-bromophenyl)-6-(2-hydroxyethoxy)-4-pyrimidinyl-N'-propyl sulfamide (100 g) in tetrahydrofuran (500 mL) was added to sodamide (18 g) in tetrahydrofuran (1500 mL) at 25-30° C. over a period of 45 min and stirred for 10 min. 5-bromo-2-chloropyrimidine (44.5 g) was added to the above reaction mass at 25-30° C. and stirred for 10 mins. The reaction mass was heated to 40-50° C. and stirred for 2.5 hrs. The reaction mass was then cooled to 25-30° C.; sodamide (18 g) and 5-bromo-2-chloropyrimidine (44.5 g) was added to it. The reaction mass was heated to 40-50° C. and stirred for 2.5 hrs. Then the reaction mass was cooled to 25-30° C. and pH was adjusted to 2.5 with aqueous hydrochloric acid and stirred for 15 mins. The solvent from the reaction mass was distilled off under vacuum at 45° C. Methylene chloride (1000 mL) followed by water (500 mL) was added to the reaction mass and stirred for 15 mins. The organic and aqueous layers were separated and the aqueous layer extracted with methylene chloride. Organic layers were combined, washed with water, 5% sodium bicarbonate followed by water and sodium chloride solution. The organic layer was concentrated completely under vacuum at below 45° C. Then the reaction mass was cooled to 25-30° C., methylene chloride (130 mL) was added and heated to 35-40° C. for complete dissolution. Methanol (1000 mL) was added to the reaction mass at 35-40° C., then heated to 55-60° C. and stirred for 45 min at reflux. The reaction mass was cooled to 25-30° C. and stirred for an hour. The solid obtained was filtered, washed with methanol and dried at 50-55° C. for 6 hrs to get the title compound. Yield: 95 g; Purity by HPLC: 99.8%; Formula (VII): <0.1%

Example-11: Purification of Macitentan

Macitentan (100 g) was dissolved in methylene chloride (500 mL) at 25-35° C. The reaction mass was subjected to carbon treatment and filtered through dicalcite bed. The filtrate was concentrated under vacuum at below 45° C. The obtained residue was dissolved in methylene chloride (180 ml) at 35-40° C. Methanol (1500 mL) was added to the reaction mass at 35-40° C. then heated to 40-45° C. and stirred for 45 mins. The reaction mass was cooled to 25-35° C. and stirred for 90 mins. The solid obtained was filtered, washed with methanol and dried under vacuum at 50-55° C. for 6 hrs to get pure macitentan. Yield: 77 g; Purity by HPLC: 99.9%.

Comparative Example: Preparation of Macitentan

N-5-(4-bromophenyl)-6-(2-hydroxyethoxy)-4-pyrimidinyl-N'-propylsulfamide (10 g) was added to sodium hydride (1.39 g) in tetrahydrofuran (200 mL) at 24-27° C. under nitrogen atmosphere and stirred for 10 min. 5-bromo-2-chloropyrimidine (4.48 g) was added to the above reaction mass at 25-30° C. and stirred for 5 mins. The reaction mass was heated to 60-65° C. and stirred for 2 hrs. The reaction mass was cooled to 30-35° C.; sodium hydride (1.39 g) and 5-bromo-2-chloropyrimidine (4.48 g) was added to the reaction mass. The reaction mass was heated to 60-65° C. and stirred for 2 hrs. The reaction mass was cooled to 24-27° C. and 10% aqueous citric acid was added and stirred for 10 mins. Ethyl acetate (300 mL) was added to the reaction mass and stirred for 10 mins. The organic and aqueous layers were separated and extracted the aqueous layer with ethyl acetate. Organic layers were combined, washed with water and 5% sodium bicarbonate solution followed by water and sodium chloride solution. The organic layer was dried over sodium sulfate and concentrated under vacuum at 45-47° C. The reaction mass was stripped off with hexane; hexane (100 mL) was added to it and stirred for an hour. The reaction mass was filtered, washed with hexane and suck dried. Methanol (100 mL) was added to the above solid at 24-27° C. The reaction mass was heated to 63-67° C. and stirred for an hour. The reaction mass was cooled to 25-30° C. and stirred for an hour. The solid obtained was filtered, washed with methanol and dried under vacuum at 40-45° C. for 6 hrs to get the title compound. Yield: 10.1 g; Purity by HPLC: 99.58%; Formula (VII): 0.27%

Purification: Methanol (100 mL) was added to the above obtained macitentan (10.1 g). The reaction mass was heated to 63-67° C. and stirred for an hour; then the reaction mass was cooled to 25-30° C. and stirred for an hour. The solid obtained was filtered, washed with methanol and dried under vacuum at 40-45° C. for 6 hrs. Yield: 9.5 g; Purity by HPLC: 99.73%; Formula (VII): 0.16%

Example-12: Purification of Macitentan

Methylene chloride (8.5 mL) was added to the macitentan (8.5 g containing 0.16% of Formula-VII) obtained as above at 24-27° C. The reaction mass was heated to 38-42° C. for dissolution. Methanol (85 mL) was added to the reaction mass and stirred for an hour at 24-27° C. The solid obtained was filtered, washed with methanol and dried under vacuum at 40-45° C. for 6 hrs to get the pure title compound. Yield: 7.1 g; Purity by HPLC: 99.97%; Formula (VII): <0.1%

Example-13: Preparation of Methylene Chloride Solvate of Macitentan

A mixture of macitentan (5 g) and methylene chloride (5 ml) was stirred for 10 mins at 25-30° C. Methylene chloride (7 mL) was added to the reaction mass at 25-30° C. and the obtained solution was stirred for 15 mins. The reaction mass was then cooled to 0-5° C. and stirred for 45 mins. The obtained solid was filtered, washed with methylene chloride and dried at 50° C. under vacuum for 4 hrs to get the title compound.

Yield: 2.3 g $^1$H NMR Data: $^1$H NMR (CDCl$_3$): δ 0.94 (t, 3H, J=7.5 Hz), 1.50-1.66 (m, 2H), 2.90-3.02 (m, 2H), 4.61 (dd, 2H, J=2.4 & 5.1 Hz), 4.71 (dd, 2H, J=3.6 & 6.6 Hz), 5.29 (s, 2H), 5.61 (t, NH, J=6.2 Hz), 6.90 (s, NH), 7.10-7.19 (m, 2H), 7.52-7.60 (m, 2H), 8.46 (s, 1H), 8.48 (s, 2H)

The NMR is set forth in FIG. 1.
The XRPD is set forth in FIG. 2.
The DSC is set forth in FIG. 3.
The TGA is set forth in FIG. 4.

We claim:

1. An improved process for the preparation of macitentan of formula (I),

I and pharmaceutically acceptable salts thereof, comprising the steps of:

a) reacting 4-bromophenyl acetic acid alkyl ester of formula (II),

II wherein R is a C$_{1-4}$ alkyl, with dialkyl carbonate in presence of a base and a solvent to obtain a compound of formula (III),

III wherein R is a C$_{1-4}$ alkyl;

b) reacting the compound of formula (III) with formamidine or a salt thereof to obtain a compound of formula (IV),

IV c) reacting the compound of formula (IV) with a reactive group source and optionally in presence of a solvent to obtain a compound of formula (V), wherein Rg represents a reactive group;

d) reacting the compound of formula (V) with N-propyl sulfamoyl amide or a salt thereof, in a solvent and optionally in presence of a base to obtain a compound of formula (VI), e) reacting the compound of formula (VI) with ethylene glycol in presence of a base to obtain a compound of formula (VII), f) condensing the compound of formula (VII) with a compound of formula (VIII)

wherein Rg represents a reactive group, in presence of a base and a solvent to obtain macitentan of formula (I); and g) purifying the macitentan of formula (I), wherein the base used in step a) is selected from the group consisting of alkali metal amides, alkali metal oxide bases, and mixtures thereof, wherein the base used in step e) is selected from one of sodamide, potassium amide, and mixtures thereof, and is added in more than one lot, and wherein purifying macitentan in step g) comprises dissolving the macitentan of formula (I) in a chloro solvent followed by adding an alcohol solvent.

2. The process of claim 1, wherein the base used in step a) is one of sodamide and potassium amide.

3. The process of claim 1, wherein the solvent in step a) is one of di-tert-butylether, diethylether, diisopropylether, di-n-butylether, 1,4-dioxane, methyltert-butylether, ethylisoproylether, ethyltert-butylether, tetrahydrofuran, 2-methyltetrahydro furan, anisole, dimethoxyethane, and mixtures thereof.

4. The process of claim 1, wherein the reactive group source in step c) is one of $POCl_3$, $PCl_3$, $PCl_5$, $PBr_3$, and $POBr_3$.

5. The process of claim 1, wherein the solvent in step c) is one of acetonitrile, propionitrile, butyronitrile, isobutyronitrile, benzonitrile, chloroform, 1,2-dichloroethane, toluene, xylene, and mixtures thereof.

6. The process of claim 1, wherein the solvent used in step d) is one of dimethylsulfoxide, dimethylformamide, dimethylacetamide, acetonitrile, chlorobenzene, isopropylacetate, tetrahydrofuran, dioxane and mixtures thereof.

7. The process of claim 1, wherein the base used in step d) is one of sodium tert-butoxide, potassium tert-butoxide, sodium hydride, potassium hydride, sodium methoxide, potassium methoxide, sodium ethoxide, triethyl amine, and ethyldiisopropyl amine.

8. The process of claim 1, wherein the base used in step e) is one of sodium hydroxide, potassium hydroxide, sodium methoxide, sodium ethoxide, potassium tert-butoxide, sodium carbonate, potassium carbonate, sodamide, potassium amide, and mixtures thereof.

9. The process of claim 1, wherein the base used in step f) is sodamide.

10. The process of claim 1, wherein the solvent used in step f) is one of di-tert-butylether, diethylether, diisopropylether, di-n-butylether, 1,4-dioxane, methyltert-butyl ether, ethylisoproylether, ethyltert-butylether, tetrahydrofuran, 2-methyl tetrahydrofuran, anisole, dimethoxyethane, dimethyl formamide, and mixtures thereof.

11. The process of claim 1, wherein in step g) the chloro solvent is methylene chloride and the alcohol solvent is methanol.

* * * * *